(12) United States Patent
Fanara et al.

(10) Patent No.: US 6,699,502 B1
(45) Date of Patent: Mar. 2, 2004

(54) PHARMACEUTICAL COMPOSITIONS FOR CONTROLLED RELEASE OF ACTIVE SUBSTANCES

(75) Inventors: Domenico Fanara, Wanze (BE); Monique Berwaer, Ham-sur-Heure-Nalinnes (BE); Anne Bouquelle, Jurbise (BE); Michel Deleers, Linkebeek (BE)

(73) Assignee: UCB, S.A., Brussels (BE)

( * ) Notice: Subject to any disclaimer, the term of this patent is extended or adjusted under 35 U.S.C. 154(b) by 820 days.

(21) Appl. No.: 09/381,044

(22) PCT Filed: Mar. 13, 1998

(86) PCT No.: PCT/BE98/00033

§ 371 (c)(1),
(2), (4) Date: Sep. 29, 1999

(87) PCT Pub. No.: WO98/41194

PCT Pub. Date: Sep. 24, 1998

(30) Foreign Application Priority Data

Mar. 14, 1997 (BE) .............................. 9700225

(51) Int. Cl.$^7$ ............................. A61K 9/14; A61K 9/24; A61K 9/20
(52) U.S. Cl. ....................... 424/484; 424/468; 424/464; 424/465; 424/472; 424/488
(58) Field of Search ................. 424/464, 465, 424/468, 472, 488, 484

(56) References Cited

FOREIGN PATENT DOCUMENTS

| EP | 0 396 404 | 11/1990 |
|----|-----------|---------|
| WO | 94 06416 | 3/1994 |
| WO | 94 09761 | 5/1994 |

*Primary Examiner*—Thurman K. Page
*Assistant Examiner*—Amy E. Pulliam
(74) *Attorney, Agent, or Firm*—Wenderoth, Lind & Ponack, L.L.P.

(57) ABSTRACT

The present invention is directed a pharmaceutical composition which can be administered orally, allowing for the controlled release of at least one active substance. The composition includes at least one active substance, between 5 and 60% by weight, relative to the total weight of the composition, of at least one excipient, selected from inert matrices, hydrophilic matrices, lipid matrices, mixtures of inert matrices and of lipid matrices, and mixtures of hydrophilic matrices and of inert matrices, with the exception of mixtures including a polyacrylic acid and at least one hydrophilic matrix of the cellulose type; and between 5 and 50% by weight, relative to the total weight of the composition, of at least one alkalinizing agent soluble in an aqueous phase under physiological pH conditions, selected from alkali or alkaline-earth metal hydroxides, carbonates, bicarbonates, phosphates, sodium borate and basic salts of organic acids. The invention further includes a process for preparation of the composition, multi-layered pharmaceutical compositions including at least one layer of the inventive composition, and processes for producing same.

10 Claims, 5 Drawing Sheets

FIGURE 1 - pseudoephedrine

FIGURE 4 - hydrocodone bitartrate

FIGURE 5 - trapidil

PHARMACEUTICAL COMPOSITIONS FOR CONTROLLED RELEASE OF ACTIVE SUBSTANCES

The present invention relates to pharmaceutical compositions which can be administered orally, allowing the controlled release of pharmaceutically active sub-stances, and to methods of preparing these pharmaceutical compositions.

One of the objectives currently sought in the development of pharmaceutical compositions which can be administered orally is to control the release of pharmaceutically active substances so that they can be administered in a few daily doses, ideally in a single daily dose.

The release of active substances during oral administration can be controlled by means of matrix-type pharmaceutical compositions. Depending on the excipients used, it is possible to identify three types of matrix inert, hydrophilic and lipophilic matrices. Mixed matrices can also be created by combining excipients for these various types of matrix.

The inert matrices comprise excipients essentially belonging to the class of thermoplastic polymers. They are inert towards biological tissues, other excipients in the formulation and the active substance. They are insoluble and indigestible in the fluids of the gastrointestinal tract. Among these, there may be mentioned polyvinyl chloride, polyethylene, vinyl acetate/vinyl chloride copolymers, polymethylmethacrylates, polyamides, silicones, ethyl cellulose, polystyrene and the like. They generally use a concentration ranging from 20 to 95%.

The hydrophilic matrices comprise gelling excipients which can be divided into three classes: the cellulose derivatives (hydroxypropyl methylcellulose, hydroxyethyl cellulose, hydroxypropyl cellulose, methylcellulose and the like), the noncellulose polysaccharides (galactomannans, guar gum, carob gum, gum arabic, sterculia gum, agar, alginates and the like) and the acrylic acid polymers (carbopols 934P and 974P and the like). They are generally used at a concentration of 20 to 700%.

The lipid matrices comprise four types of fatty excipients: glycerides (mono-, di- or triglycerides: stearin, palmitin, laurin, myristin, hydrogenated castor or cottonseed oils, precirol and the like), fatty acids and alcohols (stearic, palmitic or lauric acids; stearyl, cetyl or cetostearyl alcohols, and the like), fatty acid esters (monostearates of propylene glycol and of sucrose, sucrose distearate and the like) and waxes (white wax, cachalot wax and the like). They are generally used at a concentration of 10 to 50%.

The presence of matrix-type excipients in pharmaceutical compositions makes it possible, in a number of cases, to slow down the release of the active substances by entrapment. However, these matrix-type excipients do not always make it possible to sufficiently slow down the release of the active substance or to obtain the desired ideal release profiles.

For example, when the matrix-type pharmaceutical composition contains a substance which must imperatively be released in the stomach, the release of the active substance over sufficiently long periods depends not only on the type of excipients used in the composition, but also on the residence time of the pharmaceutical composition in the stomach. Accordingly, several documents mention the use of floating matrix tablets.

In particular, patent EP 205336 describes pharmaceutical compositions for the controlled release of active substances comprising a mixed matrix obtained from a mixture of ethers of cellulose and of a polyacrylic acid, of one of its derivatives or of their pharmaceutically acceptable salts, and comprising, in addition, from 10 to 50% by weight, relative to the total weight of matrix excipients, of effervescent foaming agent. The effervescent foaming agent makes it possible to cause the pharmaceutical composition to float in the gastric fluid, thereby increasing the residence time in the stomach. The effervescent foaming agent is an alkali or alkaline-earth metal bicarbonate which is preferably used in combination with an organic acid.

However, the floating in the gastric fluid does not allow other problems observed in the context of the control of the release of active substances from the matrix pharmaceutical compositions to be resolved.

Indeed, the quantities of matrix excipient necessary for adequate prolonged release of the active ingredient can prove to be too high and can make the production of the dosage form impossible or too costly.

Moreover, the release of some active substances greatly depends on the pH. For example, some active substances are not at all released in the stomach, but in other areas of the gastrointestinal tract. In addition, for the same area of the gastrointestinal tract, the release profile will be different depending on whether or not the composition is administered together with a meal. For the active substances whose release depends on the ambient pH, it is therefore desirable to find novel matrix compositions which make it possible to regulate the rate of release so that the active substance can be released at the same rate regardless of the pH of the medium.

Finally, it is very common for the profile of release of an active ingredient from a matrix form to be irregular over time, that is to say that the kinetics of release is not of the zero order but is a function of the square root of the time. A zero order kinetics of release corresponds to a regular and constant release over time and is highly desirable in order to ensure a regular and long-lasting therapeutic effect.

In parallel, it is increasingly therapeutically advantageous to be able to simultaneously administer by the oral route an active substance released immediately after administration, and the same or a second active substance released gradually and regularly after administration. In the case where the same active substance is simultaneously administered for immediate release and for prolonged release, this makes it possible to rapidly release a sufficient dose of active substance to trigger the desired effect and to maintain this effect by a gradual and prolonged release of the same active substance. In the case where an active substance is released immediately and another active substance is released gradually, this makes it possible to obtain combined therapeutic effects by means of two active substances having very different pharmacokinetic profiles.

In this context, international patent application WO 94/09761 describes a slow release oral composition comprising a) a matrix core comprising
   pseudoephedrine sulfate
   hydroxypropylmethylcellulose
   ethylcellulose
   dibasic calcium phosphate
   povidone
   silicon dioxide
   magnesium stearate
and
b) a coating on the matrix core comprising
   loratadine
   hydroxypropylmethylcellulose
   polyethylene glycol 400
   polyethylene glycol 3350.

European patent application EP-A-0 396 404 describes a slow release oral composition comprising
a) a matrix core comprising
  ibuprofen
  pseudoephedrine
  swellable hydrophilic polymers, such as hydroxypropylmethylcellulose
  excipient such as dibasic calcium phosphate
  lubricant such as magnesium stearate,
and
b) a coating on the core comprising
  loratadine
  hydrophilic polymer
  other excipients.

In this context, orally administrable solid pharmaceutical compositions combining, in a single unit, a portion exhibiting immediate release and a portion exhibiting delayed release have been described. However, these compositions require methods of preparation which are technically very sophisticated and/or do not allow the desired release profiles to be obtained for all the active substances.

We have now just discovered, surprisingly, novel pharmaceutical compositions which can be administered orally, allowing the controlled release of pharmaceutically active substances such that a satisfactory therapeutic effect is observed over fairly long periods, for example in only one or even two daily doses.

In particular, the compositions according to the present invention do not require excessive quantities of matrix excipients and allow regular and continuous release of active substances over periods of at least 12 hours.

In addition, we have also just discovered that these new controlled-release pharmaceutical compositions can be used in combination with an immediate-release pharmaceutical composition for the same or for another active substance, in a single unit intended to be administered orally.

The present invention therefore relates to pharmaceutical compositions which can be administered orally, allowing the controlled release of at least one active substance, comprising
a) the said at least one active substance,
b) between 5 and 60% by weight, relative to the total weight of the composition, of at least one excipient, selected from inert matrices, hydrophilic matrices, lipid matrices, mixtures of inert matrices and of lipid matrices, mixtures of hydrophilic matrices and of lipid matrices, mixtures of hydrophilic matrices and of inert matrices, with the exception of mixtures comprising a polyacrylic acid and at least one hydrophilic matrix of the cellulose type;
c) between 5 and 50% by weight, relative to the total weight of the composition, of at least one alkalinizing agent soluble in an aqueous phase under physiological pH conditions, selected from alkali or alkaline-earth metal hydroxides, carbonates, bicarbonates and phosphates, sodium borate as well as the basic salts of organic acids.

The present invention is in particular illustrated by FIGS. 1 to 5.

The pharmaceutical compositions according to the present invention comprise matrix excipients chosen from inert, hydrophilic and lipophilic matrices.

Examples of inert matrices which can be used according to the present invention are: polyvinyl chloride, polyethylene, vinyl acetate/vinyl chloride copolymers, polymethylmethacrylates, polyamides, silicones, ethyl cellulose, polystyrene and the like.

Examples of hydrophilic matrices which can be used according to the present invention are: cellulose derivatives (hydroxypropyl methylcellulose, hydroxyethyl cellulose, hydroxypropyl cellulose, methylcellulose and the like), non-cellulose polysaccharides (galactomannans, guar gum, carob gum, gum arabic, sterculia gum, agar, alginates and the like) and acrylic acid polymers (carbopols 934P and 974P and the like). The hydrophilic matrices preferably used according to the present invention are hydroxypropyl celluloses, such as METHOCEL K or E. The content of hydroxypropyl methylcellulose-type excipients in the compositions according to the present invention is preferably between 5 and 60% by weight relative to the total weight of the composition.

Examples of lipid matrices which can be used according to the present invention are: glycerides (mono-, di- or triglycerides: stearin, palmitin, laurin, myristin, hydrogenated castor or cottonseed oils, precirol and the like), fatty acids and alcohols (stearic acid, palmitic acid, lauric acid; stearyl alcohol, cetyl alcohol, cetostearyl alcohols, and the like), fatty acid esters (monostearates of propylene glycol and of sucrose, sucrose distearate and the like) and waxes (white wax, cachalot wax and the like).

The matrix excipients may also be in the form of a mixture. However, the pharmaceutical compositions of the invention do not comprise mixtures comprising a polyacrylic acid and at least one hydrophilic matrix of the cellulose type.

The alkalinizing agent which can be used according to the present invention should be soluble in the aqueous phase under physiological pH conditions so as to produce the desired effect. The alkalinizing agent may be chosen from alkali or alkaline-earth metal hydroxides, carbonates, bicarbonates and phosphates, sodium borate as well as basic salts of organic acids (example: sodium citrate). On the other hand, salts not soluble in water under physiological pH conditions, such as magnesium stearate or dibasic calcium phosphate, are not suitable according to the present invention.

The quantity of alkalinizing agent present in the pharmaceutical compositions according to the present invention is ideally from 5 to 50% by weight relative to the total weight of the composition.

As regards the active substances which may be present in the compositions according to the present invention, they may be of a wide variety of types.

They may be chosen from vasoconstrictors, antihistamines, analgesics, antitussives and the like. The applicant has in particular observed that the invention is particularly suited to active substances whose free base is less soluble in water than its pharmaceutically acceptable salts. Nonlimiting examples of such active substances are pseudoephedrine, ephedrine, phenylephrine, phenylpropanolamine, trapidil, hydrocodone, cetirizine, efletirizine, hydroxyzine, meclozine, buclizine, pentoxyverine, codeine, morphine, their optical isomers or their pharmaceutically acceptable salts.

As regards the dose of active substance used, it depends on the effective dose and may therefore vary within very wide limits depending on the said active substance.

In addition to the above-mentioned components, the pharmaceutical compositions according to the present invention may also contain other excipients such as diluents (example: emcompress, lactose and the like), binders (avicel, starches, polyvinylpyrrolidone and the like), disintegrants (starches and modified starches, cellulose derivatives, alginic derivatives, pectins and the like), lubricants (talc, magnesium stearate, colloidal silica and the like), taste-masking agents (α-cyclodextrin, β-cyclodextrin, γ-cyclodextrin and their alkylated derivatives), flavourings or colourings as well as coating agents (example: cellulose derivatives, methacrylic resins, polyvinyl chloride, nylons and the like).

The pharmaceutical compositions according to the present invention are generally provided in a solid form. It is important to underline that the beneficial effects of the invention are observed regardless of the presentation of the galenic form. The pharmaceutical compositions according to the present invention are provided in the form of tablets, granules, microgranules and the like, these forms being coated or otherwise.

The controlled-release pharmaceutical compositions according to the present invention can be prepared by various conventional methods known to persons skilled in the art.

Generally, the pharmaceutical compositions according to the present invention are prepared by a process comprising the following successive steps:

i. preparation of a homogeneous mixture containing components a, b and c and the other excipients optionally present;

ii. tabletting of the homogeneous mixture obtained in step i, optionally after granulation.

The tabletting may be of various types and is ideally carried out by direct tabletting. The optional granulation in step ii may be carried out either by the wet route or by the dry route, or alternatively by melt-granulation.

According to a specific embodiment of the invention, the controlled-release pharmaceutical compositions according to the invention are used in combination with one or more pharmaceutical compositions allowing immediate release of active substances. When these two types of compositions are present in the same unit, this makes it possible to obtain, in a single administration, both the immediate release of a first active substance and the prolonged release of the same or of a second active substance.

Accordingly, the present invention also relates to pharmaceutical compositions which can be administered orally, comprising A. at least one layer comprising an active substance and excipients which allow immediate release of the said active substance after administration, and B. at least a second layer which allows the controlled release of the same or of a second active substance, comprising the said same or second active substance, at least one matrix-type excipient and at least one alkalinizing agent.

As regards layer A, the excipients allowing immediate release of the active substance may be chosen from diluents (emcompress, lactose and the like), binders (Avicel, starches, polyvinylpyrrolidone and the like), disintegrants (starches and modified starches, cellulose derivatives, alginic derivatives, pectins and the like), lubricants (talc, magnesium stearate, colloidal silica and the like), taste-masking agents (α-cyclodextrin, β-cyclodextrin, γ-cyclodextrin and their alkylated derivatives), flavourings or colourings.

Such combined pharmaceutical compositions can be prepared according to various methods known to persons skilled in the art.

More particularly, these combined pharmaceutical compositions may be provided in the form of a tablet in which at least one layer A is stuck to at least one layer B. In this case, such pharmaceutical compositions may be prepared by a process comprising the following successive steps:

1) preparation of separate homogeneous mixtures from the components of layers A and B, and 2) tabletting of the homogeneous mixtures obtained in 1) in a multilayer tabletting machine.

Optionally, the tabletting step 2) may be preceded by a step of granulating the homogeneous mixtures obtained in step 1).

The multilayer tabletting machines which make it possible to prepare this type of tablet are Courtoy, Manesty, Hata, Fette, Killian type multilayer tabletting machines and the like.

The multilayer tablets are particularly well suited to cases of combinations of active substances for which very specific beneficial therapeutic effects have recently been obtained, for example, pseudoephedrine/cetirizine, hydrocodone/acetaminophen, immediate release hydrocodone/prolonged release hydrocodone.

The following examples illustrate the present invention without, however, limiting it. In the examples which follow, the percentages are expressed by weight relative to the total weight of the compositions.

EXAMPLE 1

Reducing the Quantity of Matrix Excipient

Controlled-release pseudoephedrine tablets A, B and C containing 120 mg doses were prepared by direct tabletting from homogeneous mixtures having, respectively, the compositions presented in Table 1.

The A tablets contain 16% of matrix excipient and 14.25% of alkalinizing agent. They have a mean weight of 281.03 mg and a hardness of 104 N.

The B and C tablets, for their part, contain no alkalinizing agent and contain 40% and 50% of matrix excipient respectively. They have a mean weight of 298.3 mg and 402.25 mg respectively, and their respective degrees of hardness are 118 N and 137 N.

TABLE 1

Composition of the A, B and C tablets

| | mg/tablet | | |
|---|---|---|---|
| Constituents | A | B | C |
| Pseudoephedrine.HCl | 120 | 120 | 120 |
| Methocel K15M CR | 45 | 120 | — |
| Methocel K100M CR | — | — | 200 |
| Na$_2$CO$_3$, anhydrous | 40 | — | — |
| Avicel pH 102 | 70.8 | 55.5 | 74 |
| Aerosil 200 | 1.4 | 1.5 | 2 |
| Magnesium stearate | 2.8 | 3 | 4 |

The kinetics of release of pseudoephedrine from these 3 types of tablet was determined in vitro with the aid of the USP 23 dissolution apparatus No. 1 (23rd edition of the American Pharmacopoeia). The tablets are placed in the basket which is subjected to 50 revolutions per minute. The dissolution medium consists of 500 ml of distilled water kept at 37° C. Every hour, for 12 hours, a sample is taken from the dissolution medium and the pseudoephedrine is assayed by HPLC. The results of these assays are presented in Table 2.

TABLE 2

Percentage release of pseudoephedrine.

| Time (h) | A | B | C |
|---|---|---|---|
| 0 | 0 | 0 | 0 |
| 1 | 31.87 | 41.56 | 38.81 |
| 2 | 46.04 | 57.89 | 51.69 |
| 3 | 56.4 | 71.4 | 62.43 |
| 4 | 65.07 | 81.43 | 72.02 |
| 5 | 75.41 | 86.34 | 77.65 |
| 6 | 75.95 | 90.44 | 83.53 |
| 7 | 77.7 | 93.01 | 85.21 |
| 8 | 79.6 | 94.16 | 88.48 |
| 10 | 82.82 | 96.21 | 92.16 |
| 12 | 85.36 | 94.05 | 93.07 |

The results of Table 2 show that fairly similar release profiles are observed in the three cases, the slowest release being observed for the A tablets. This shows that a very good control of release can be obtained with less matrix excipient when an alkalinizing agent is present in the composition.

The A, B and C tablets were also the subject of a test of bioavailability in man over a period of 32 hours. In this test, the profiles of bioavailability obtained with the A, B and C tablets were compared with the bioavailability profile obtained by administering immediate release gelatin capsules of pseudoephedrine containing 60 mg doses, administered after an interval of 6 hours.

Eight healthy subjects (18 to 45 year old men) participated in this crossover study, each subject receiving 4 forms with a "wash-out" period of 7 days between the two administrations. Blood samples were taken from the subjects over 32 hours according to the following schemes:

matrix tablets: 0, 0.5, 1, 1.5, 2, 3, 4, 5, 6, 7, 8, 10, 12, 16, 24 and 32 hours;

gelatin capsules: 0, 0.5, 1, 1.5, 2, 3, 4, 5, 6,6.5, 7, 7.5, 8, 9, 10, 12, 16, 24 and 32 hours.

The pseudoephedrine levels were determined by a validated HPLC method (UV detection).

Figure 1:
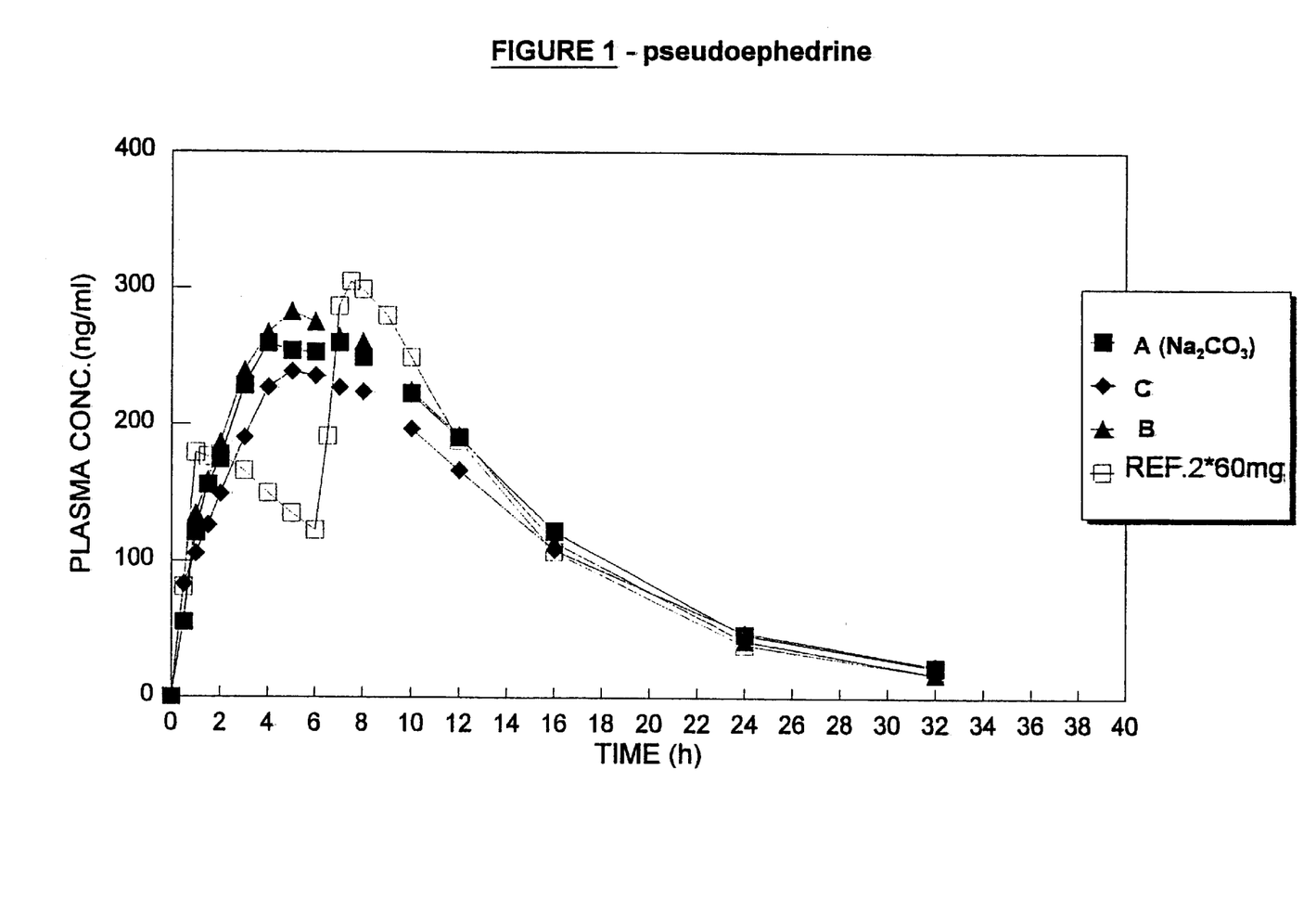
FIG. 1: pseudoephedrine bioavailability profiles obtained with cetirizine (immediate release)/pseudoephedrine (controlled release) bilayer tablets.

The results of this bioavailability study are presented in FIG. 1 and in Table 3, in which AUC represents the area under the curve, $C_{max}$ represents the maximum concentration detected and $T_{max}$ represents the time necessary to obtain $C_{max}$.

TABLE 3

Bioavailability of pseudoephedrine in man.

| | Gelatin capsules | Tablets (120 mg) | | |
|---|---|---|---|---|
| | (2 × 60 mg) | A | B | C |
| AUC (µg.h/ml) | 3672 | 4019 | 4028 | 3683 |
| $C_{max}$ (µg/ml) | 391 | 276 | 295 | 259 |
| $T_{max}$ (h) | 1.5 | 4.5 | 5.0 | 5.0 |

The results of this bioavailability study show that much more regular release profiles are obtained with pharmaceutical compositions comprising matrix excipients containing 120 mg doses compared with that obtained with two administrations of immediate-release tablets containing 60 mg doses.

Moreover, the active substance is released in a comparable manner for the A, B and C tablets. This example illustrates the fact that, to obtain an adequate prolonged release of the active substance, a much smaller quantity of matrix excipient (16% instead of 40% or 50%) is sufficient when this excipient is combined with an alkalinizing agent.

EXAMPLE 2

Effect of Coating

Controlled-release pseudoephedrine tablets containing 120 mg doses and containing 15.4% of Methocel K15M CR and 13.7% of sodium carbonate were prepared by direct tabletting from a homogeneous mixture having the composition presented in Table 4 (D tablets).

TABLE 4

D Tablets.

| Constituents | mg/tablet |
|---|---|
| Pseudoephedrine.HCl | 120 |
| Methocel K15M CR | 45 |
| $Na_2CO_3$, anhydrous | 40 |
| Avicel pH 102 | 82.5 |
| Aerosil 200 | 1.4 |
| Magnesium stearate | 2.8 |

The D tablets have a mean weight of 292.5 mg. A portion of these tablets was coated with Opadry OY-B-28920 (polyvinyl alcohol, lecithin, xanthan gum, titanium dioxide, talc). The kinetics of in vitro release of pseudoephedrine from the coated or uncoated D tablets was determined in the same manner as in Example 1. The results are presented in Table 5.

TABLE 5

Percentage release of pseudoephedrine.

| Time (h) | Uncoated | Coated |
|---|---|---|
| 0 | 0 | 0 |
| 1 | 33.7 | 30.4 |
| 2 | 47.5 | 45.6 |
| 3 | 57.9 | 56.5 |
| 4 | 65.8 | 65.7 |
| 5 | 71.9 | 72.0 |
| 6 | 77.1 | 76.8 |
| 7 | 80.7 | 80.2 |
| 8 | 83.4 | 83.1 |

The results presented in Table 5 show that the coating does not affect the kinetics of release of the active substance.

EXAMPLE 3

Effect of Various Alkalinizing Agents

Controlled-release pseudoephedrine tablets containing 180 mg doses and containing 30% of Methocel K15M CR and 30% of sodium carbonate (E), sodium bicarbonate (F) or potassium hydrogen phosphate (G) were prepared by direct tabletting from homogeneous mixtures having the compositions presented in Table 6.

TABLE 6

E, F and G tablets.

| | mg/tablet | | |
|---|---|---|---|
| Constituents | E | F | G |
| Pseudoephedrine.HCl | 180 | 180 | 180 |
| Methocel K15M CR | 180 | 180 | 180 |
| Na$_2$CO$_3$, anhydrous | 180 | — | — |
| NaHCO$_3$ | — | 180 | — |
| K$_2$HPO$_4$ | — | — | 180 |
| Avicel pH 102 | 51 | 51 | 51 |
| Aerosil 200 | 3 | 3 | 3 |
| Magnesium stearate | 6 | 6 | 6 |

The kinetics of in vitro release of pseudoephedrine for the E, F and G tablets, obtained in the same manner as in Example 1 with the baskets rotating at 100 rpm, are collated in Table 7.

TABLE 7

Percentage release of pseudoephedrine.

| Time (h) | E | F | G |
|---|---|---|---|
| 0 | 0 | 0 | 0 |
| 1 | 17.1 | 29.2 | 28.9 |
| 2 | 23.3 | 45.6 | 45.2 |
| 3 | 28.9 | 57.7 | 56.2 |
| 4 | 34.5 | 67.3 | 65.1 |
| 5 | 39.1 | 74.9 | 73.3 |
| 6 | 44.1 | 81.6 | 79.8 |
| 7 | 49.2 | 86.1 | 85.2 |

The results of Table 7 show that a prolonged release is obtained with the three alkalinizing agents used, the effect being more marked with sodium carbonate.

EXAMPLE 4

Pseudoephedrine/alkalinizing Double-layer Tablets

Double-layer tablets containing 120 mg doses of controlled-release pseudoephedrine and 5 mg of immediate-release cetirizine were prepared in the following manner (H tablets).

Two separate homogeneous mixtures (H$_A$ and H$_B$) were prepared from the compositions presented in Tables 8 and 9.

Mixtures H$_A$ and H$_B$ were then tabletted in a multilayer tabletting machine to give double-layer tablets in which the layers are stuck to each other. These tablets were then coated with Opadry OY-B-28920 (polyvinyl alcohol, lecithin, xanthan gum, titanium dioxide, talc).

In these tablets, the prolonged-release layer contains 16.1% of matrix excipient and 14.3% of sodium carbonate.

TABLE 8

Mixture H$_A$.

| Constituents | mg/tablet |
|---|---|
| Cetirizine.2HCl | 5 |
| Tablettose | 41.3 |
| Avicel pH 102 | 22.65 |
| Aerosil 200 | 0.35 |
| Magnesium stearate | 0.7 |

TABLE 9

Mixture H$_B$.

| Constituents | mg/tablet |
|---|---|
| Pseudoephedrine.HCl | 120 |
| Methocel K15M CR | 45 |
| Na$_2$CO$_3$, anhydrous | 40 |
| Aerosil 200 | 1.4 |
| Magnesium stearate | 2.8 |

The kinetics of in vitro release of pseudoephedrine and of cetirizine for the H tablets, obtained in the same manner as in Example 1 with baskets rotating at 100 rpm, are collated in Table 10.

TABLE 10

Percentage release of pseudoephedrine and cetirizine.

| Time (h) | Pseudoephedrine | Cetirizine |
|---|---|---|
| 0 | 0 | 0 |
| 0.25 | 11.2 | 80.2 |
| 0.5 | 21.4 | 82.7 |
| 0.75 | 32.0 | 86.0 |
| 1 | 37.8 | 86.6 |
| 2 | 58.2 | 89.7 |
| 4 | 83.7 | 93.4 |
| 6 | 97.9 | 97.5 |
| 8 | 102.4 | 99.5 |
| 10 | 104.6 | 101.2 |
| 12 | 105.8 | 101.8 |

EXAMPLE 5

Effect of the pH

Controlled-release trapidil tablets I and J containing 300 mg doses were prepared by direct tabletting from homogeneous mixtures having the compositions collated in Table 11.

The I and J tablets contain 33.3% of matrix excipient; the I tablets contain no alkalinizing agent and the J tablets contain 12.5% of alkalinizing agent.

TABLE 11

Compositions of the I and J tablets.

| | mg/tablet | |
|---|---|---|
| Constituents | I | J |
| Trapidil | 300 | 300 |
| Methocel K100M CR | 200 | 200 |
| Na$_2$CO$_3$, anhydrous | — | 75 |
| Avicel pH 102 | 91 | 16 |
| Aerosil 200 | 3 | 3 |
| Magnesium stearate | 6 | 6 |

The mean weights and the degrees of hardness of the I and J tablets are 605.3 mg and 125 N (I) and 597.7 mg and 79 N (J), respectively. The kinetics of in vitro release of trapidil were determined according to the method described in example 1 using two dissolution media: a 0.1 N solution of hydrochloric acid and a solution of phosphate buffer at pH 7.5. The speed of rotation of the baskets was 100 rpm. The results of this study are presented in Table 12, as well as in FIGS. 2 and 3.

TABLE 12

Percentage release of trapidil as a function of the ambient pH.

| | 0.1 N HCl | | Buffer pH 7.5 | |
|---|---|---|---|---|
| Time (h) | I | J | I | J |
| 0 | 0 | 0 | 0 | 0 |
| 1 | 26.7 | 12.5 | 13.5 | 13.8 |
| 2 | 39.5 | 21.4 | 20.8 | 21.9 |
| 3 | 49.6 | 29.3 | 26.6 | 28.4 |
| 4 | 58.2 | 36.3 | 31.6 | 33.8 |
| 5 | 64.9 | 42.3 | 35.9 | 38.7 |
| 6 | 71.2 | 47.8 | 40.1 | 43.1 |
| 7 | 76.8 | 53.2 | 43.3 | 46.9 |
| 8 | 83.1 | 59.1 | 45.7 | 50.5 |
| 10 | 90.4 | 67.7 | 53.5 | 57.2 |
| 12 | 94.6 | 74.6 | 59.1 | 62.6 |
| 15 | 100.5 | 86.3 | 67.0 | 70.2 |
| 17 | 100.0 | 89.9 | 70.9 | 73.8 |

Figure 2:
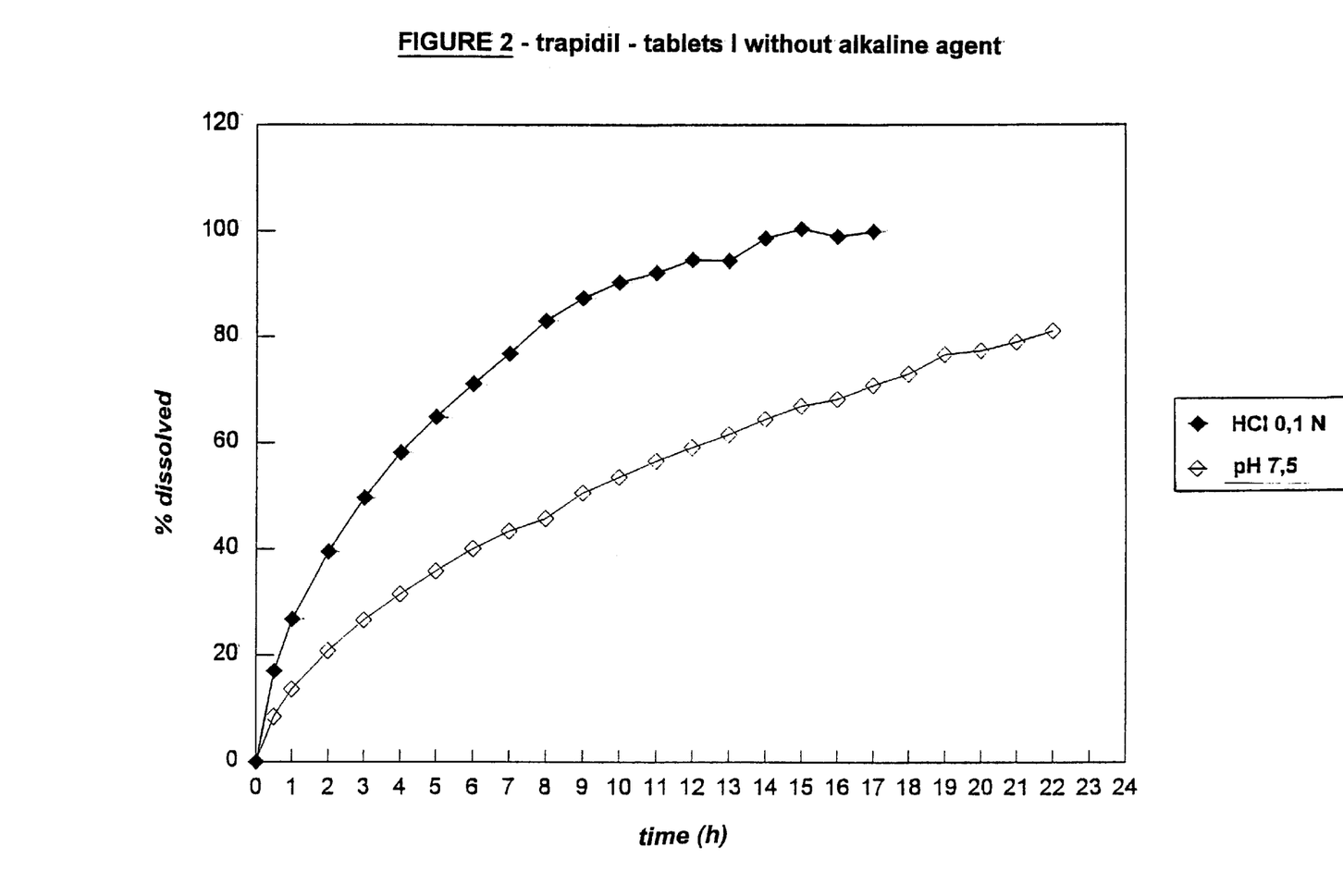
FIG. 2: kinetics of in vitro release of trapidil; matrix tablets without alkalinizing agent.

FIG. 2 and the results presented in Table 12 for the I tablets show that these tablets exhibit very different release kinetics depending on the pH. These results show that a controlled and prolonged release cannot be obtained in a strongly acidic medium when there is no alkalinizing agent in the pharmaceutical composition.

Figure 3:
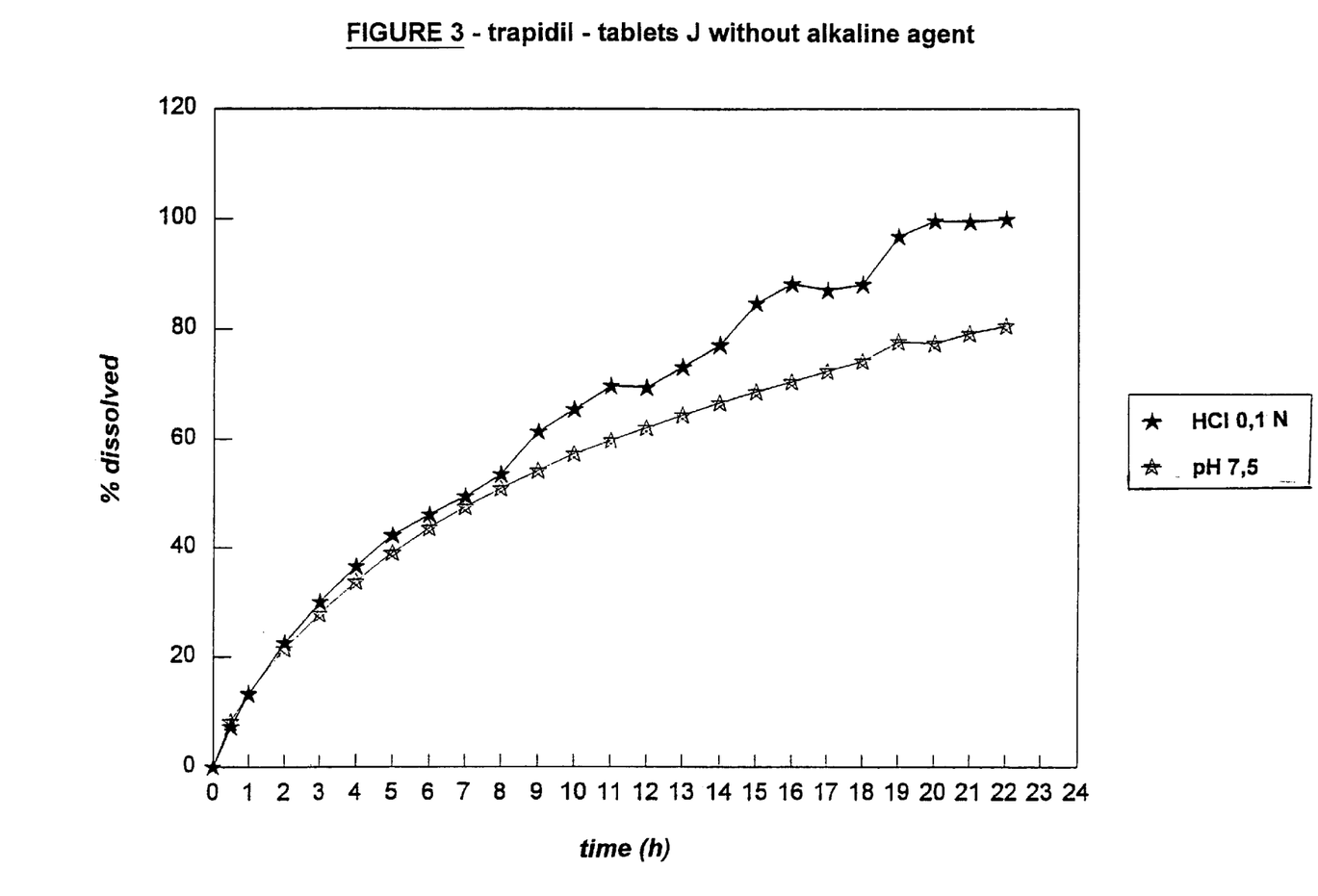
FIG. 3: kinetics of in vitro release of trapidil; matrix tablets with alkaling agent.

FIG. 3 and the results presented in Table 12 for the J tablets show that a prolonged release of the active substance may very well be obtained in a strongly acidic medium when an g agent is present in the pharmaceutical composition.

EXAMPLE 6

Linearization of the Kinetics of Release

Controlled-release hydrocodone tablets K and L containing 15 mg doses were prepared by direct tabletting from homogeneous mixtures having the compositions collated in Table 13. The K tablets contain 56.7% of matrix excipient and contain no alkalinizing agent; the L tablets contain 43.3% of matrix excipient and 13.5% of alkalinizing agent.

TABLE 13

Compositions of the K and L tablets.

| | mg/tablet | |
|---|---|---|
| Constituents | K | L |
| Hydrocodone bitartrate | 15 | 15 |
| Methocel K100M CR | 85 | 65 |
| $Na_2CO_3$, anhydrous | — | 20 |
| Avicel pH 102 | 48 | 48 |
| Aerosil 200 | 0.5 | 0.5 |
| Magnesium stearate | 1.5 | 1.5 |

The kinetics of in vitro release of hydrocodone from the K and L tablets were determined with the aid of the USP 23 dissolution apparatus No. 2. The tablets are placed in the dissolution container. The speed of rotation of the paddles is 100 revolutions per minute. The dissolution medium consists of 500 ml of a phosphate buffer solution at pH 5.8. Samples were taken over 12 hours from the dissolution medium and the hydrocodone is assayed by HPLC. The results of this study are presented in Table 14 and FIG. 4.

TABLE 14

Percentage release of hydrocodone.

| Time (h) | K | L |
|---|---|---|
| 0 | 0 | 0 |
| 1 | 24.9 | 5.4 |
| 2 | 41.8 | 9.2 |
| 4 | 65.0 | 17.7 |
| 6 | 80.7 | 31.5 |
| 8 | 91.5 | 45.8 |
| 10 | 97.8 | 57.6 |
| 12 | 103.7 | 63.1 |

Figure 4:
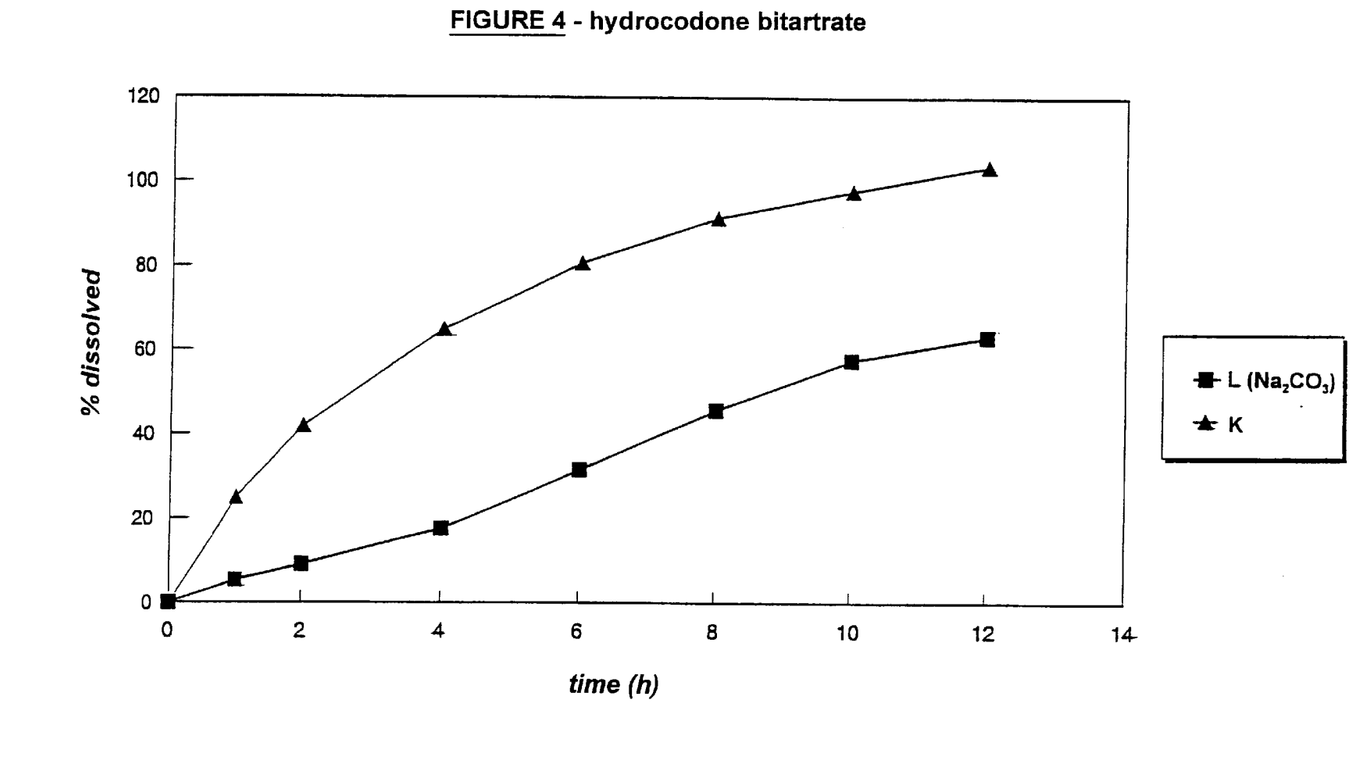
FIG. 4: kinetics of in vitro release of hydrocodones; matrix tablets with and without alkanilizing agent.

The results presented in Table 14 show that the presence of alkalinizing agent in the composition slows the release of the active substance. In addition, as shown in FIG. 4, the kinetics of release is linearized, that is to say that the rate of release remains constant over time.

Another test carried out under similar conditions and by assaying the hydrocodone by UV spectroscopy also showed a constant rate of release over 18 hours. Furthermore, the release of the active substance was complete after 18 hours.

EXAMPLE 7

Hydrocodone/hydrocodone Double-layer Tablets

Double-layer tablets containing 15 mg doses of hydrocodone consisting of a controlled-release layer containing a 10 mg dose of hydrocodone and an immediate-release layer containing a 15 mg dose of hydrocodone were prepared in the following manner (M tablets).

Two separate homogeneous mixtures ($M_A$ and $M_B$) were prepared from the compositions presented in Tables 15 and 16.

The mixtures $M_A$ and $M_B$ were then tabletted in a multilayer tabletting machine to give double-layer tablets in which the two layers are stuck to each other. In these tablets, the prolonged-release layer contains 43.3% of Methocel K100M CR and 13.3% of sodium carbonate.

TABLE 15

Mixture $M_A$.

| Constituents | mg/tablet |
|---|---|
| Hydrocodone bitartrate | 5 |
| Tablettose | 28.2 |
| Avicel pH 102 | 16.1 |
| Aerosil 200 | 0.3 |
| Magnesium stearate | 0.4 |

TABLE 16

Mixture $M_B$.

| Constituents | mg/tablet |
|---|---|
| Hydrocodone bitartrate | 10 |
| Methocel K100M CR | 43.3 |
| $Na_2CO_3$, anhydrous | 13.3 |
| Avicel pH 102 | 32.1 |
| Aerosil 200 | 0.3 |
| Magnesium stearate | 1 |

The kinetics of in vitro release of hydrocodone for the M tablets were determined with the aid of the USP 23 dissolution apparatus No. 1. The speed of rotation of the baskets was 100 revolutions per minute. The dissolution medium consisted of 500 ml of a phosphate buffer solution at pH 5.8. The hydrocodone was assayed as in Example 6. The results are presented in Table 17.

TABLE 17

Percentage release of hydrocodone.

| Time (h) | Hydrocodone |
|---|---|
| 0 | 0 |
| 1 | 35.0 |
| 2 | 41.5 |
| 4 | 64.6 |
| 6 | 82.2 |
| 8 | 89.1 |
| 10 | 94.3 |
| 12 | 101.0 |

The results presented in Table 17 show that 35% of hydrocodone was already released after 1 hour, which corresponds to the hydrocodone content in the immediate-release layer (33.3% of the total dose). Next, the release of hydrocodone continues gradually and regularly according to a kinetics comparable to that observed in Example 6.

EXAMPLE 8

Hydrocodone-inert Matrix Tablets

Controlled-release hydrocodone tablets N and O containing 15 mg doses and containing cellulose acetate as inert matrix excipient were prepared by direct tabletting from homogeneous mixtures having the compositions collated in Table 18. The N tablets contain 54% of inert matrix excipient and 13.3% of alkalinizing agent and the O tablets contain 54% of inert matrix excipient and contain no alkalinizing agent.

TABLE 18

Compositions of the N and O tablets.

| | mg/tablet | |
|---|---|---|
| Constituents | N | O |
| Hydrocodone bitartrate | 15 | 15 |
| Cellulose acetate CA398-10NF | 81 | 81 |
| Emcompass | 32 | 52 |
| Sodium carbonate | 20 | 0 |
| Aerosil 200 | 0.5 | 0.5 |
| Magnesium stearate | 1.5 | 1.5 |

The kinetics of release of hydrocodone from these two types of tablet was determined in vitro with the aid of the USP 23 dissolution apparatus No. 1. The tablets are placed in the basket which is subjected to 100 revolutions per minute. The dissolution medium consisted of 500 ml of a phosphate buffer solution at pH 5.8. The hydrocodone was assayed as in Example 6. The results are presented in Table 19.

TABLE 19

Percentage release of hydrocodone.

| | Hydrocodone | |
|---|---|---|
| Time (h) | N | O |
| 0 | 0 | 0 |
| 1 | 9.57 | 48.88 |
| 2 | 21.44 | 78.24 |
| 4 | 27.61 | 91.24 |
| 6 | 34.05 | 100.94 |
| 8 | 51.93 | 101.07 |
| 10 | 58.44 | 95.60 |
| 12 | 81.21 | 99.64 |

The results presented in Table 19 show that the presence of alkalinizing agent in the composition slows the release of the active substance. In addition, as in Example 6, the kinetics of release is linearized.

EXAMPLE 9

Hydrocodone-lipid Matrix Tablets

Controlled-release hydrocodone tablets P and Q containing 15 mg doses and containing CUTINA HR as lipid matrix excipient were prepared by direct tabletting from homogeneous mixtures having the compositions collated in Table 20. The P tablets contain 30.2% of lipid matrix excipient and 13.3% of alkalinizing agent and the Q tablets contain 30.2% of lipid matrix excipient and contain no alkalinizing agent.

TABLE 20

Compositions of the P and Q tablets.

| | mg/tablet | |
|---|---|---|
| Constituents | P | Q |
| Hydrocodone bitartrate | 15 | 15 |
| Cutina HR | 45.3 | 45.3 |
| Avicel pH 102 | 67.8 | 87.7 |
| Sodium carbonate | 20 | 0 |
| Aerosil 200 | 0.5 | 0.5 |
| Magnesium stearate | 1.5 | 1.5 |

The kinetics of release of hydrocodone from these two types of tablet was determined in vitro with the aid of the USP 23 dissolution apparatus No. 1. The tablets are placed in the basket which is subjected to 100 revolutions per minute. The dissolution medium consisted of 500 ml of a phosphate buffer solution at pH 5.8. The hydrocodone was assayed as in Example 6. The results are presented in Table 21.

TABLE 21

Percentage release of hydrocodone.

| | Hydrocodone | |
|---|---|---|
| Time (h) | P | Q |
| 0 | 0 | 0 |
| 1 | 5.91 | 58.76 |
| 2 | 12.50 | 84.46 |
| 3 | 23.05 | 91.96 |
| 4 | 29.01 | 91.47 |
| 6 | 52.07 | 101.84 |

TABLE 21-continued

Percentage release of hydrocodone.

| Time (h) | Hydrocodone | |
|---|---|---|
| | P | Q |
| 8 | 68.96 | 102.63 |
| 10 | 80.92 | 103.37 |
| 12 | 90.73 | 104.92 |

The results presented in Table 21 show that the presence of alkalinizing agent in the composition slows the release of the active substance. In addition, as in Example 6, the kinetics of release is linearized.

EXAMPLE 10

Hydrocodone-mixed Matrix Tablets

Controlled-release hydrocodone tablets R and S containing 15 mg doses and containing a mixture of METHOCEL K100M CR and EUDRAGIT RSPM as matrix excipients were prepared by direct tabletting from homogeneous mixtures having the compositions collated in Table 20. The R tablets contain 43.3% of matrix excipient and 13.3% of alkalinizing agent and the S tablets contain 43.3% of matrix excipient and contain no alkalinizing agent.

TABLE 22

Compositions of the R and S tablets.

| | mg/tablet | |
|---|---|---|
| Constituents | R | S |
| Hydrocodone bitartrate | 15 | 15 |
| Methocel K100M CR | 52.5 | 52.5 |
| Eudragit RSPM | 12.5 | 12.5 |
| Avicel pH 102 | 48 | 68 |
| Sodium carbonate | 20 | 0 |
| Aerosil 200 | 0.5 | 0.5 |
| Magnesium stearate | 1.5 | 1.5 |

The kinetics of release of hydrocodone from these two types of tablet was determined in vitro with the aid of the USP 23 dissolution apparatus No. 1. The tablets are placed in the basket which is subjected to 100 revolutions per minute. The dissolution medium consisted of 500 ml of a phosphate buffer solution at pH 5.8. The hydrocodone was assayed as in Example 6. The results are presented in Table 23.

TABLE 23

Percentage release of hydrocodone.

| Time (h) | Hydrocodone | |
|---|---|---|
| | R | S |
| 0 | 0 | 0 |
| 1 | 9.10 | 26.05 |
| 2 | 18.12 | 42.80 |
| 3 | 27.81 | 49.76 |
| 4 | 38.13 | 59.32 |
| 6 | 63.41 | 70.16 |

TABLE 23-continued

Percentage release of hydrocodone.

| Time (h) | Hydrocodone | |
|---|---|---|
| | R | S |
| 8 | 81.76 | 78.13 |
| 10 | 88.12 | 83.22 |
| 12 | 101.69 | 88.73 |

The results presented in Table 23 show that the presence of alkalinizing agent in the composition slows the release of the active substance. In addition, as in Example 6, the kinetics of release is linearized.

EXAMPLE 11

Coated Matrix Tablets of Efletirizine

Controlled-release efletirizine tablets T, U and V containing 30 mg doses were prepared by wet granulation of the active ingredient with emcompress. Their composition is collated in Table 24.

TABLE 24

Compositions of the T, U and V tablets.

| | mg/tablet | | |
|---|---|---|---|
| Constituents | T | U | V |
| Efletirizine.2HCl | 30 | 30 | 30 |
| Methocel K15M CR | 70 | 40 | 33.3 |
| Emcompress | 77 | 36.3 | 35 |
| Sodium bicarbonate | 20 | 12 | 0 |
| Aerosil 200 | 1 | 0.7 | 0.7 |
| Magnesium stearate | 2 | 1 | 1 |
| Opadry Y1-7000 | 6 | 3.6 | 3 |

The kinetics of release of efletirizine from these three types of tablet was determined in vitro with the aid of the USP 23 dissolution apparatus No. 1. The tablets are placed in the basket which is subjected to 100 revolutions per minute. Three dissolution media were tested: water and buffered solutions at pH 4.5 and 7.5. The efletirizine was assayed by HPLC for the buffer solution at pH 4.5 and by UV spectroscopy for the other solutions. The results are given in Table 25.

TABLE 25

Percentage release of efletirizine.

| | Efletirizine | | | | | | | | |
|---|---|---|---|---|---|---|---|---|---|
| | T | | | U | | | V | | |
| Time (h) | pH 4.5 | Water | pH 7.5 | pH 4.5 | Water | pH 7.5 | pH 4.5 | Water | pH 7.5 |
| 0 | 0 | 0 | 0 | 0 | 0 | 0 | 0 | 0 | 0 |
| 1 | 11.79 | 10.35 | 15.70 | 25.97 | 17.83 | 36.82 | 17.67 | 20.07 | 13.12 |
| 2 | 20.18 | 18.83 | 25.77 | 35.36 | 29.32 | 48.33 | 18.04 | 36.15 | 22.04 |
| 4 | 35.47 | 33.07 | 41.47 | 51.97 | 48.38 | 63.88 | 29.47 | 54.13 | 37.40 |
| 6 | 47.82 | 44.88 | 53.80 | 65.44 | 62.62 | 75.90 | 39.18 | 71.23 | 50.82 |
| 8 | 59.05 | 54.85 | 64.10 | 75.70 | 74.68 | 84.48 | 49.17 | 85.08 | 62.16 |
| 12 | 75.84 | 70.97 | 80.37 | 91.40 | 90.25 | 96.57 | 67.55 | 97.37 | 80.69 |
| 16 | 87.23 | 82.88 | 91.73 | 100.64 | 100.32 | 104.03 | 89.74 | 102.45 | 93.58 |
| 24 | 102.62 | 98.08 | 104.72 | 106.47 | 104.95 | 109.42 | 105.35 | 102.27 | 104.21 |

The results presented in Table 25 show that for the V tablet, which contains no alkalinizing agent, the kinetics of release is strongly dependent on the pH. For the other two types of tablet, this difference is greatly reduced.

EXAMPLE 12

Coated Matrix Tablets of Trapidil

Hydrophilic matrices W, X and Y containing 300 mg doses of trapidil containing an alkalinizing agent were prepared by wet granulation of sodium bicarbonate, lactose and povidone; their composition is collated in Table 26.

TABLE 26

Compositions of the W, X and Y tablets.

| | mg/tablet | | |
|---|---|---|---|
| Constituents | W | X | Y |
| Trapidil | 300 | 300 | 300 |
| Methocel K15M CR | 0 | 0 | 200 |
| Methocel E4M CR | 150 | 0 | 0 |
| Natrosol 250 HHX | 0 | 150 | 0 |
| Sodium bicarbonate | 60 | 60 | 60 |
| Avicel PH 101 | 50 | 100.8 | 0 |
| Lactose 100 mesh | 32 | 32 | 32 |
| Aerosil standard | 3 | 3.25 | 3 |
| Magnesium stearate | 3 | 1.95 | 3 |
| Povidone K30 | 2 | 2 | 2 |
| Opadry Y1-7000 | 18 | 20 | 18 |

The W, X and Y tablets were subjected to a test of bioavailability in man over a period of 24 hours, each volunteer receiving 2 tablets at time 0. The bio-availability profiles obtained with the W, X and Y tablets were compared with the profile obtained by 3 administrations at 6-hour intervals, of 200 mg immediate-release gelatin capsules (reference). The profile was also determined after a single administration of an aqueous solution containing 200 mg of trapidil.

Eight healthy subjects (18 to 45 year old men) participated in this crossover study, each subject receiving the 5 forms with a "wash-out" period of 7 days between two administrations.

Blood samples were collected from the subjects over 24 hours according to the following schemes:

oral solution: 0, 0.33, 0.5, 0.67, 0.83, 1, 1.5, 2, 4 and 6 hours;

gelatin capsule: 0, 0.33, 0.67, 1, 2, 4 and 6 hours after each of the 3 administrations, matrix tablets: 0, 0.5, 1, 2, 4, 8, 12, 16, 20 and 24 hours.

Figure 5:
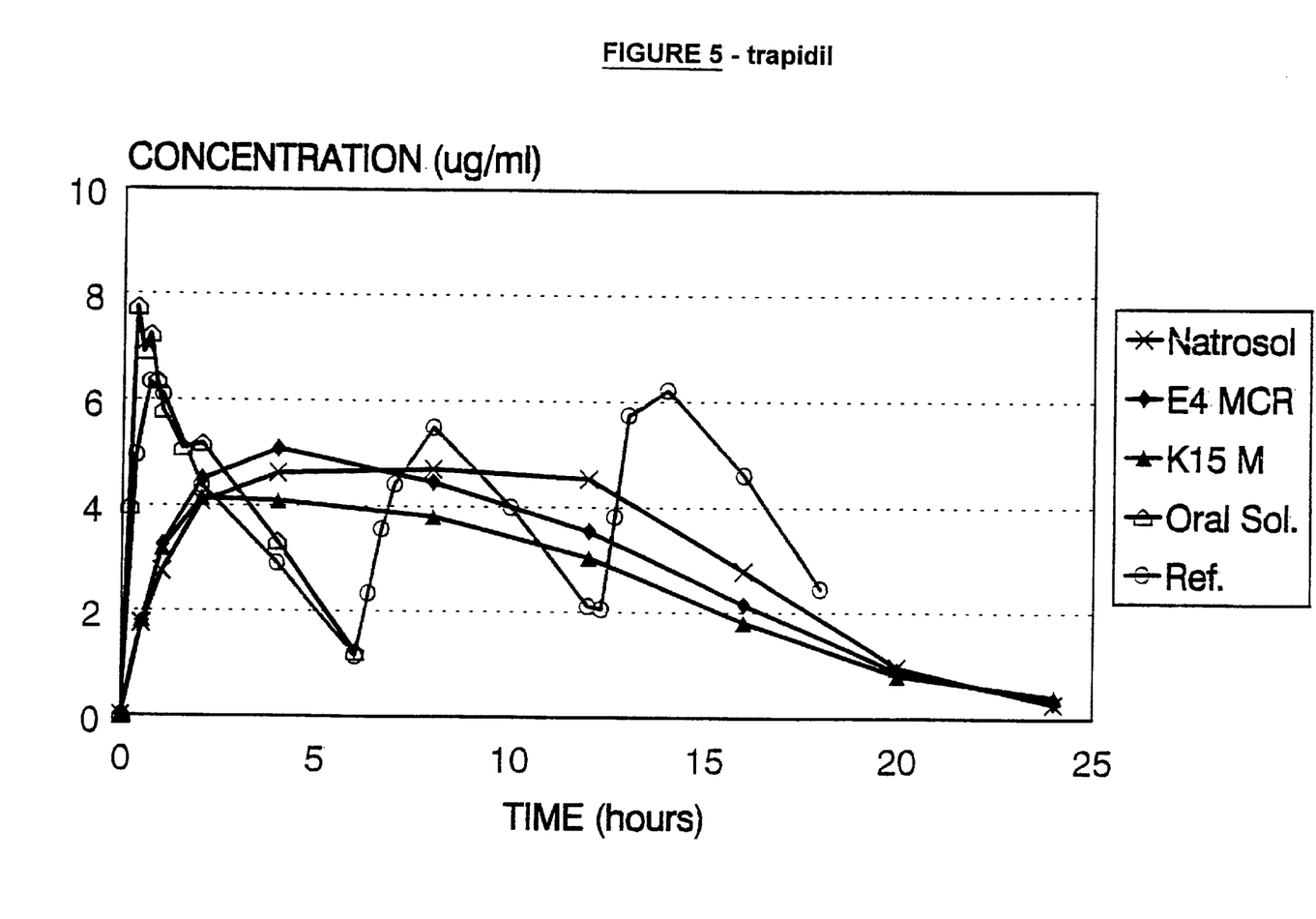
FIG. 5: profiles of bioavailability of trapidil obtained with coated matrix tablets.

The results of this study are presented in FIG. 5 and in Table 27, in which AUC represents the area under the curve, $C_{max}$ represents the maximum concentration detected and $t_{max}$ represents the time necessary to obtain $C_{max}$.

TABLE 27

Bioavailability of trapidil in man.

| | | Tablets | | |
|---|---|---|---|---|
| | Gelatin capsules | W | X | Y |
| $AUC_{0-24h}$ ($\mu$g.h/ml) | 74.3 | 64.9 | 69.4 | 55.7 |
| $C_{max}$ ($\mu$g/ml) | 7.55 | 5.05 | 5.07 | 4.34 |
| $T_{max}$ (h) | 1 | 4 | 10 | 3 |

The results of this study show that the matrix tablets provide prolonged release of the active substance. Compared with the multiple administration of rapid-release gelatin capsules, the X tablet gives particularly advantageous results with a prolonged $t_{max}$. The $C_{max}$ is reduced by about 30%, thus avoiding blood concentration peaks, but showing a plateau which extends over more than 12 hours for a practically equivalent absorption of active ingredient.

What is claimed is:

1. A pharmaceutical composition which can be administered orally, allowing the controlled release of at least one active substance, comprising:

a) the said at least one active substance, b) between 5 and 60% by weight, relative to the total weight of the composition, of at least one excipient, selected from the group consisting of inert matrices; hydrophilic matrices, lipid matrices, mixtures of inert matrices and of lipid matrices, and mixtures of hydrophilic matrices and of inert matrices, with the exception of mixtures comprising a polyacrylic acid and at least one hydrophilic matrix of the cellulose type; and c) between 5 and 50% by weight, relative to the total weight of the composition, of at least one alkalinizing agent soluble in an aqueous phase under physiological pH conditions, selected from the group consisting of alkali or alkaline-earth metal hydroxides, carbonates, bicarbonates, phosphates, sodium borate and basic salts of organic acids.

2. The pharmaceutical composition according to claim 1, wherein the active substance is selected from the group consisting of pseudoephedrine, efletirizine, trapidil, hydrocodone, their optical isomers and their pharmaceutically acceptable salts.

3. The pharmaceutical composition according to claim 1, wherein the matrix excipient is hydroxypropyl methylcellulose.

4. The pharmaceutical composition according to claim 1, which comprises, in addition, one or more additional pharmaceutically acceptable excipients.

5. The pharmaceutical composition according to claim 4, wherein the said one or more additional pharmaceutically acceptable excipients is selected from the group consisting of diluents, binders, disintegrants, lubricants, taste-masking agents, flavourings, colorings and coating agents.

6. A process for preparing a pharmaceutical composition according to claim 1, which comprises the following successive steps:

(i) preparing a homogeneous mixture containing components a, b, and c according to claim 1 and additional excipients optionally present; and (ii) tabletting the homogeneous mixture obtained in step (i), optionally after granulation.

7. A pharmaceutical composition which can be administered orally, allowing the immediate release of a first active substance and the prolonged release of the same or of a second active substance, comprising:

A. at least one layer comprising an active substance and excipients which allow immediate release of the said active substance after administration, and B. at least one second layer which allows the controlled release of the same or of a second active substance, this layer being a pharmaceutical composition according to claim 1.

8. The pharmaceutical composition according to claim 7, wherein the immediate-release layer A is contacting the prolonged-release layer B.

9. A process for the preparation of a pharmaceutical composition according to claim 7, which comprises the following successive steps:

(1) preparing separate homogeneous mixtures from the components of layers A and B, and (2) tabletting the mixture obtained in step (1) in a multi-layer tabletting machine.

10. The process of preparation according to claim 9, wherein the tabletting step (2) is preceded by a step of granulating the homogeneous mixtures obtained in step (1).

* * * * *